(12) United States Patent
Hofmann et al.

(10) Patent No.: US 7,008,900 B1
(45) Date of Patent: *Mar. 7, 2006

(54) DOUBLE METAL CYANIDE CATALYSTS FOR PRODUCING POLYETHER POLYOLS

(75) Inventors: Jörg Hofmann, Krefeld (DE); Pieter Ooms, Krefeld (DE); Pramod Gupta, Bedburg (DE); Walter Schäfer, Leichlingen (DE); John Lohrenz, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/890,889

(22) PCT Filed: Jan. 31, 2000

(86) PCT No.: PCT/EP00/00727

§ 371 (c)(1),
(2), (4) Date: Aug. 7, 2001

(87) PCT Pub. No.: WO00/47649

PCT Pub. Date: Aug. 17, 2000

(30) Foreign Application Priority Data

Feb. 11, 1999 (DE) ............................... 199 05 611

(51) Int. Cl.
*B01J 27/26* (2006.01)
(52) U.S. Cl. .................................................. 502/175
(58) Field of Classification Search ............... 528/403, 528/408, 409, 414, 415; 502/100, 174, 175
See application file for complete search history.

(56) References Cited

U.S. PATENT DOCUMENTS

| | | | |
|---|---|---|---|
| 3,404,109 A | 10/1968 | Milgrom et al. ............ 260/611 |
| 3,829,505 A | 8/1974 | Herold et al. .............. 260/611 |
| 3,941,849 A | 3/1976 | Herold ...................... 260/607 |
| 5,158,922 A | 10/1992 | Hinney et al. .............. 502/175 |
| 5,470,813 A | 11/1995 | Le-Khac .................... 502/175 |
| 5,545,601 A | 8/1996 | Le-Khac .................... 502/156 |
| 5,627,120 A | 5/1997 | Le-Khac .................... 502/156 |
| 5,998,327 A * | 12/1999 | Hofmann et al. ........... 502/175 |
| 6,018,017 A | 1/2000 | Le-Khac .................... 528/421 |
| 6,291,388 B1 * | 9/2001 | Hofmann et al. ........... 502/154 |
| 6,323,375 B1 * | 11/2001 | Hofmann et al. ........... 568/613 |
| 6,586,566 B1 * | 7/2003 | Hofmann et al. ........... 528/425 |
| 6,696,383 B1 * | 2/2004 | Le-Khac et al. ............ 502/175 |
| 6,764,978 B1 * | 7/2004 | Grosch et al. .............. 502/175 |
| 6,780,813 B1 * | 8/2004 | Hofmann et al. ........... 502/175 |
| 6,797,665 B1 * | 9/2004 | Le-Khac .................... 502/175 |
| 6,835,687 B1 * | 12/2004 | Hofmann et al. ........... 502/175 |
| 6,852,663 B1 * | 2/2005 | Ooms et al. ................ 502/175 |
| 6,867,162 B1 * | 3/2005 | Le-Khac et al. ............ 502/175 |

FOREIGN PATENT DOCUMENTS

| | | |
|---|---|---|
| EP | 0046523 | 3/1982 |
| EP | 0892002 | 1/1999 |
| EP | 0 700 949 | 3/1999 |
| JP | 4-145123 | 5/1992 |
| WO | WO 99/19063 | * 4/1999 |
| WO | WO 99/46042 | * 9/1999 |

OTHER PUBLICATIONS

U.S. Appl. No. 10/717,093, filed Nov. 19, 2003: Le-Khac et al.*
U.S. Appl. No. 10/138,209, filed May 3, 2002: Ooms et al.*
U.S. Appl. No. 10/133,287, filed Apr. 26, 2002: Hofmann et al.*
U.S. Appl. No. 10/129,579, filed May 7, 2002: Ooms et al.*
U.S. Appl. No. 10/493,608, filed Apr. 23, 2004: Bohres et al.*
Ullmanns Encyclopedia der industriellen Chemie, vol. A21, (month unavailable) 1992, pp. 670-671, Polyols.
Kunstsaffhandbuch, vol. 7 Polyurethane, 3$^{rd}$ edition, (month unavailable) 1993 pp. 25-32, Herstellungsmethoen fur Polyurethane, Dr. D. Dietrich, Dr. H.G. Schmelzer.
Kunststaffhandbuch, vol. 7 Polyurethane, 3$^{rd}$ edition (month unavailable) 1993 pp. 57-67, Rohstoffe, Dr. W. Diller, Dr. P. Gupta, Dr. P. Haas, Dr. K. Schauerte, Dr. R. Sundermann, Dr. K. Uhlig.
Nachr. Chem. Tech. Lab. 43 (month unavailable) 1995. pp. 1047-1055, Gallensauren: Wiederentdeckt, Gunther Wess, Alfons Enhsen, und Werner Kramer.
Rompp-Lexikon Naturstoffe, Stulgast, New York, (month unavailable) 1997 pp. 248-250.

* cited by examiner

*Primary Examiner*—Michael J. Feely
(74) *Attorney, Agent, or Firm*—Joseph C. Gil; Lyndanne M. Whalen; John E. Mrozinski, Jr.

(57) ABSTRACT

The invention provides new double metal cyanide (DMC) catalysts for preparing polyetherpolyols by the polyaddition of alkylene oxides to starter compounds which contain active hydrogen atoms, wherein the catalyst comprises a) double metal cyanide compounds, b) bile acids or their salts, esters or amides and c) organic complex ligands. The catalysts according to the invention show greatly increased activity during preparation of a polyetherpolyol.

19 Claims, No Drawings

DOUBLE METAL CYANIDE CATALYSTS FOR PRODUCING POLYETHER POLYOLS

The invention provides new double metal cyanide (DMC) catalysts for preparing polyetherpolyols by the polyaddition of alkylene oxides to starter compounds which contain active hydrogen atoms.

Double metal cyanide (DMC) catalysts for the polyaddition of alkylene oxides to starter compounds containing active hydrogen atoms are known (e.g. from U.S. Pat. No. 3, 404,109, U.S. Pat. No. 3,829,505, U.S. Pat. No. 3,941,849 and U.S. Pat. No. 5,158,922). The use of these DMC catalysts for preparing polyetherpolyols causes in particular a reduction in the proportion of monofunctional polyethers with terminal double bonds, so-called monools, as compared with the conventional preparation of polyetherpolyols using alkali metal catalysts such as alkali metal hydroxides. The polyetherpolyols obtained in this way may be processed to produce high quality polyurethanes (e.g. elastomers, foams, coatings). DMC catalysts are usually obtained by reacting an aqueous solution of a metal salt with an aqueous solution of a metal cyanide salt in the presence of an organic complex ligand, e.g. an ether. In a typical catalyst preparation, for example, aqueous solutions of zinc chloride (in excess) and potassium hexacyanocobaltate are mixed and then dimethoxyethane (glyme) is added to the suspension produced. After filtering and washing the catalyst with aqueous glyme solution, an active catalyst of the general formula $$Zn_3[Co(CN)_6]_2 \cdot x\ ZnCl_2 \cdot y\ H_2O \cdot z\ glyme$$

is obtained (see e.g. EP-A 700 949).

JP-A 4145123, U.S. Pat. No. 5,470,813, EP-A 700 949 EP-743 093, EP-A 761 708 and WO 97/40086 disclose DMC catalysts which further reduce the proportion of monofunctional polyethers with terminal double bonds during preparation of polyetherpolyols by using tertiary butanol as the organic complex ligand (on its own or combined with a polyether (EP-A 700 949, EP-A 761 708, WO 97/40086)). In addition, the induction time during the polyaddition reaction of alkylene oxides with corresponding starter compounds is reduced and the catalyst activity is increased by using these DMC catalysts.

The object of the present invention was to provide further improved DMC catalysts for the polyaddition of alkylene oxides to corresponding starter compounds which have increased catalyst activity as compared with the currently known catalyst types. This leads to improved economic viability of the method for preparing polyetherpolyols due to shortening the alkoxylation time. Ideally, as a result of the increased activity, the catalyst is then used in such small concentrations (25 ppm or less) that the costly procedure to separate the catalyst from the product is no longer required and the product can be used directly for polyurethane production.

Surprisingly, it has now been found that DMC catalysts which contain a bile acid or its salt, ester or amide as complex ligand have greatly increased activity during the production of polyetherpolyols.

Therefore the present invention provides a double metal cyanide (DMC) catalyst comprising a) one or more, preferably one, double metal cyanide compound, b) one or more, preferably one, bile acid or its salt, ester or amide, and c) one or more, preferably one, organic complex ligand which differs from b).

In the catalyst according to the invention, d) water, preferably 1 to 10 wt. % and/or e) one or more water-soluble metal salts, preferably 5 to 25 wt. %, of the formula (I) $M(X)_n$ from the preparation of the double metal cyanide compounds a) may optionally be contained. In formula (I) M is selected from the metals Zn(II), Fe(II), Ni(II), Mn(II), Co(II), Sn(II), Pb(II), Fe(III), Mo(IV), Mo(VI), Al(III), V(V), V(IV), Sr(II), W(IV), W(VI), Cu(II) and Cr(III). Zn(II), Fe(II), Co(II) and Ni(II) are particularly preferred. The anions X may be identical or different, preferably identical, and are preferably selected from the group of halides, hydroxides, sulfates, carbonates, cyanates, thiocyanates, isocyanates, isothiocyanates, carboxylates, oxalates or nitrates. The value of n is 1, 2 or 3.

The double metal cyanide compounds a) contained in catalysts according to the invention are the reaction products of water-soluble metal salts and water-soluble metal cyanide salts.

To prepare double metal cyanide compounds a), suitable water-soluble metal salts preferably have the general formula (I) $M(X)_n$, wherein M is selected from the metals Zn(II), Fe(II), Ni(II), Mn(II), Co(II), Sn(II), Pb(II), Fe(III), Mo(IV), Mo(VI), Al(III), V(V), V(IV), Sr(II), W(IV), W(VI), Cu(II) and Cr(III). Zn(II), Fe(II), Co(II) and Ni(II) are particularly preferred. The anions X are identical or different, preferably identical, and are preferably selected from the group of halides, hydroxides, sulfates, carbonates, cyanates, thiocyanates, isocyanates, isothiocyanates, carboxylates, oxalates or nitrates. The value of n is 1, 2 or 3.

Examples of suitable water-soluble metal salts are zinc chloride, zinc bromide, zinc acetate, zinc acetylacetonate, zinc benzoate, zinc nitrate, iron(II) sulfate, iron(II) bromide, iron(II) chloride, cobalt(II) chloride, cobalt(II) thiocyanate, nickel(II) chloride and nickel(II) nitrate. Mixtures of different water-soluble metal salts may also be used.

To prepare double metal cyanide compounds a), suitable water-soluble metal cyanide salts preferably have the general formula (II) $(Y)_a\ M'(CN)_b\ (A)_c$, wherein M' is selected from the metals Fe(II), Fe(III), Co(II), Co(III), Cr(II), Cr(III), Mn(II), Mn(III), Ir(III), Ni(II), Rh(III), Ru(II), V(IV) and V(V). M' is particularly preferably selected from the metals Co(II), Co(III), Fe(II), Fe(III), Cr(III), Ir(III) and Ni(II). The water-soluble metal cyanide salt may contain one or more of these metals. The cations Y are identical or different, preferably identical, and are selected from the group containing the alkali metal ions and alkaline earth metal ions. The anions A are identical or different, preferably identical, and are selected from the group of halides, hydroxides, sulfates, carbonates, cyanates, thiocyanates, isocyanates, isothiocyanates, carboxylates, oxalates or nitrates. The subscripts a, and also b and c are integers, wherein the values for a, b and c are selected so that the metal cyanide salt is electrically neutral: a is preferably 1, 2, 3 or 4; b is preferably 4, 5 or 6; c preferably has the value 0. Examples of suitable water-soluble metal cyanide salts are potassium hexacyanocobaltate(III), potassium hexacyanoferrate(II), potassium hexacyanoferrate(III), calcium hexacyanocobaltate(III) and lithium hexacyanocobaltate(III).

Preferred double metal cyanide compounds a), which are contained in catalysts according to the invention are compounds of the general formula (III)

$$M_x[M'_{x'}(CN)_y]_z$$

wherein M is defined in the same way as for formula (I) and M' is defined in the same way as for formula (II), and x, x', y and z are integers and selected so that the double metal cyanide compound is electrically neutral.

Preferably x=3, x'=1, y=6 and z=2.

M=Zn(II), Fe(II), Co(II) or Ni(II) and

M'=Co(III), Fe(III), Cr(III) or Ir(III).

Examples of suitable double metal cyanide compounds a) are zinc hexacyanocobaltate(III), zinc hexacyanoiridate(III), zinc hexacyanoferrate(III) and cobalt(II) hexacyanocobaltate(III). Further examples of suitable double metal cyanide compounds are given e.g. in U.S. Pat. No. 5,158,922. Zinc hexacyanocobaltate(III) is particularly preferably used.

The organic complex ligands c) contained in DMC catalysts according to the invention are known in principle and are described in detail in the prior art (see e.g. U.S. Pat. No. 5,158,922, U.S. Pat. No. 3,404,109, U.S. Pat. No. 3,829,505, U.S. Pat. No. 3,941,849, EP-A 700 949, EP-A 761 708, JP-A 4145123, U.S. Pat. No. 5,470,813, EP-A 743 093 and WO 97/40086). Preferred organic complex ligands are water-soluble, organic compounds with heteroatoms such as oxygen, nitrogen, phosphorus or sulfur, which can produce complexes with a double metal cyanide compound a). Suitable organic complex ligands are e.g. alcohols, aldehydes, ketones, ethers, esters, amides, urea, nitrites, sulfides and mixtures thereof. Preferred organic complex ligands are water-soluble aliphatic alcohols such as ethanol, isopropanol, n-butanol, i-butanol, sec.butanol and tert-butanol. Tertbutanol is particularly preferred.

The organic complex ligand is added either during preparation of the catalyst or immediately after the precipitation of double metal cyanide compound a). The organic complex ligand is usually used in excess.

DMC catalysts according to the invention contain the double metal cyanide compounds a) in amounts of 25 to 90 wt. %, preferably 30 to 85 wt. %, with respect to the amount of final catalyst and the organic complex ligands c) in amounts of 0.5 to 30 wt. %, preferably 1 to 25 wt. %, with respect to the amount of final catalyst. DMC catalysts according to the invention conventionally contain 1 to 80 wt. %, preferably 1 to 40 wt. %, with respect to the amount of final catalyst, of a bile acid or its salt, ester or amide.

Bile acids suitable for preparing catalysts according to the invention are $C_{24}$-steroid carboxylic acids, which are degradation products of cholesterol and which are generally derived from 5-cholan-24-acid by introducing—hydroxy groups at the C3, C6, C7 and C12 positions.

Preferred bile acids have the general formula

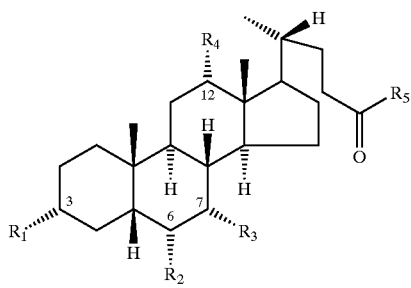

wherein $R_1$, $R_2$, $R_3$ and $R_4$, independently, represent H or OH and $R_5$ represents OH, NH—$CH_2$—COOH, NH—$CH_2$—$CH_2$—$SO_3$H, NH—$(CH_2)_3$—$N^+(CH_3)_2$ —$CH_2$—CHOH—$CH_2$—$SO_3^-$ or NH—$(CH_2)_3$—$N^+(CH_3)_2$ —$(CH_2)_3$—$SO_3^-$.

The free acids or their salts, preferably alkali or alkaline earth metal salts are suitable as well as their esters, preferably with alkyl groups with 2 to 30 carbon atoms, and their amides, preferably with alkyl groups or sulfoalkyl, sulfoalkylaminoalkyl, sulfohydroxyalkylaminoalkyl and carboxyalkyl groups, in the acid or salt form.

Examples of suitable bile acids or their salts, esters or amides are cholic acid (3α, 7α, 12α-trihydroxy-5β-cholan-24-acid; $R_1$=$R_3$=$R_4$=$R_5$=OH, $R_2$=H), the sodium salt of cholic acid (sodium cholate), lithium cholate, potassium cholate, glycocholic acid (3α,7α,12α-trihydroxy-5β-cholan-24-acid-N-[carboxymethyl]-amide; $R_1$=$R_3$=$R_4$=OH, $R_2$=H, $R_5$=NH—$CH_2$—COOH), sodium glycocholate, taurocholic acid (3α,7α,12α-trihydroxy-5β-cholan-24-acid-N-[2-sulfoethyl]-amide; $R_1$=$R_3$=$R_4$=OH, $R_2$=H, $R_5$=NH—$CH_2$—$CH_2$—$SO_3$H), sodium taurocholate, deoxycholic acid (3α,12α-dihydroxy-5β-cholan-24-acid; $R_1$=$R_4$=$R_5$=OH, $R_2$=$R_3$=H), sodium deoxycholate, potassium deoxycholate, lithium deoxycholate, glycodeoxycholic acid (3α,12α-dihydroxy-5β-cholan-24-acid-N-[carboxymethyl]-amide; $R_1$=$R_4$=OH, $R_2$=$R_3$=H, $R_5$=NH—$CH_2$—COOH), sodium glycodeoxycholate, taurodeoxycholic acid (3α,12α-dihydroxy-5β-cholan-24-acid-N-[2-sulfoethyl]-amide; $R_1$=$R_4$=OH, $R_2$=$R_3$=H, $R_5$=NH—$CH_2$—$CH_2$—$SO_3$H), sodium taurodeoxycholate, chenodeoxycholic acid (3α,7α-dihydroxy-5β-cholan-24-acid; $R_1$=$R_3$=$R_5$=OH, $R_2$=$R_4$=H), sodium chenodeoxycholate, glycochenodeoxycholic acid (3α,7α-dihydroxy-5β-cholan-24-acid-N-[carboxymethyl]-amide; $R_1$=$R_3$=OH, $R_2$=$R_4$=H, $R_5$=NH—$CH_2$—COOH), sodium glycochenodeoxycholate, taurochenodeoxycholic acid (3α,7α-dihydroxy-5β-cholan-24-acid-N-[2-sulfoethyl]-amide; $R_1$=$R_3$=OH, $R_2$=$R_4$=H, $R_5$=NH—$CH_2$—$CH_2$—$SO_3$H), sodium taurochenodeoxycholate, lithocholic acid (3α-hydroxy-5β-cholan-24-acid; $R_1$=$R_5$=OH, $R_2$=$R_3$=$R_4$=H), sodium lithocholate, potassium lithocholate, hyocholic acid (3α,6α,7α-trihydroxy-5β-cholan-24-acid; $R_1$=$R_2$=$R_3$=$R_5$=OH, $R_4$=H), sodium hyocholate, lithium hyocholate, potassium hyocholate, hyodeoxycholic acid (3α,6α-dihydroxy-5β-cholan-24-acid; $R_1$=$R_2$=$R_5$=OH; $R_3$=$R_4$=H), sodium hyodeoxycholate, lithium hyodeoxycholate, potassium hyodeoxycholate, methyl cholate, ethyl cholate, ethyl deoxycholate and methyl hyocholate.

The bile acids or their salts, esters or amides may be used individually or in the form of mixtures.

The sodium, lithium or potassium salts or the methyl or ethyl esters of cholic acid, glycocholic acid, taurocholic acid, deoxycholic acid, glycodeoxycholic acid, taurodeoxycholic acid, chenodeoxycholic acid, glycochenodeoxycholic acid, taurochenodeoxycholic acid, lithocholic acid, hyocholic acid, hyodeoxycholic acid or mixtures thereof are particularly preferably used.

Bile acids such as ursodeoxycholic acid (3α,7α-dihydroxy-5β-cholan-24-acid), 7-oxo-lithocholic acid, (3α-hydroxy-7-oxo-5β-cholan-24-acid), lithocholic acid-3-sulfate (3α-hydroxy-5β-cholan-24-acid-3-sulfate), nor-cholic acid and bisnor-cholic acid or their salts, esters or amides are also suitable.

The bile acids and their salts, esters or amides are generally well-known and are described in detail for instance in Nachr. Chem. Tech. Lab. 43 (1995) 1047, and "Römpp-Lexikon Naturstoffe" Stuttgart, N.Y. 1997, p. 248 et seq.

Any mixtures at all of the previously mentioned bile acids or their salts, esters or amides may also be used.

Analysis of the catalyst composition is conventionally performed using elemental analysis, thermogravimetry and extractive removal of the bile acid or its salt, ester or amide followed by gravimetric determination.

Catalysts according to the invention may be crystalline, partially crystalline or amorphous. Analysis of the crystallinity is conventionally performed by powder X-ray diffractometry.

Catalysts according to the invention preferably contain a) zinc hexacyanocobaltate(III)
b) a bile acid or its salt, ester or amide and
c) tert-butanol.

DMC catalysts according to the invention are conventionally prepared in aqueous solution by reacting α) metal salts, in particular of the formula (I) with metal cyanide salts in particular of the formula (II), β) organic complex ligands c) which differ from the bile acid or its salt, ester or amide and γ) the bile acid or its salt, ester or amide.

Preferably, the aqueous solutions of the metal salt (e.g. zinc chloride, used in stoichiometric excess (at least 50 mol. % with respect to the metal cyanide salt)) and the metal cyanide salt (e.g. potassium hexacyanocobaltate) are first reacted in the presence of the organic complex ligand c) (e.g. tert-butanol), wherein a suspension is produced which contains the double metal cyanide compound a) (e.g. zinc hexacyanocobaltate), water d), excess metal salt e) and the organic complex ligand c).

The organic complex ligand c) may be present in the aqueous solution of the metal salt and/or the metal cyanide salt, or it may be added directly to the suspension obtained after precipitation of the double metal cyanide compound a). It has proven advantageous to mix the aqueous solutions and the organic complex ligand c) under vigorous stirring. The suspension produced is then generally treated with the bile acid or its salt, ester or amide b). The bile acid or its salt, ester or amide b) is preferably used in a mixture with water and organic complex ligand c).

The catalyst is then isolated from the suspension using known techniques such as centrifuging or filtration. In a preferred specific variant, the isolated catalyst is then washed with an aqueous solution of the organic complex ligand c) (e.g. by resuspension followed by renewed isolation after filtration or centrifuging). In this way for example, water-soluble secondary products such as potassium chloride can be removed from the catalyst according to the invention.

The amount of organic complex ligand c) in the aqueous wash solution is preferably between 40 and 80 wt. %, with respect to the total solution. Furthermore it is advantageous to add some bile acid or its salt, ester or amide, preferably in the range between 0.5 and 5 wt. %, with respect to the total solution, to the aqueous wash solution.

In addition it is advantageous to wash the catalyst more than once. In this case e.g. the first wash process may be repeated. However, it is preferable to use non-aqueous solutions for further wash processes, e.g. a mixture of the organic complex ligand and bile acid or its salt, ester or amide.

The washed catalyst is then dried, optionally after being powdered, at temperatures of in general 20 to 100° C. and at pressures of in general 0.1 mbar to standard pressure (1013 mbar).

The present invention also provides use of the DMC catalysts according to the invention in a process for preparing polyetherpolyols by the polyaddition of alkylene oxides to starter compounds which contain active hydrogen atoms.

The alkylene oxides used are preferably ethylene oxide, propylene oxide, butylene oxide and mixtures thereof. Building up the polyether chain by alkoxylation may be performed e.g. with only one monomeric epoxide or randomly or blockwise with two or three different monomeric epoxides. More details may be obtained from "Ullmans Encyclopädie der industriellen Chemie", Vol A 21, 1992, p. 670 et seq.

The starter compounds which contain active hydrogen atoms are preferably compounds with (number average) molecular weights of 18 to 2,000 and 1 to 8 hydroxyl groups. The following may be mentioned for example: ethylene glycol, diethylene glycol, triethylene glycol, 1,2-propylene glycol, 1,4-butanediol, hexamethylene glycol, bisphenol A, trimethylolpropane, glycerol, pentaerythritol, sorbitol, cane sugar, degraded starch or water.

Advantageously, those starter compounds which contain active hydrogen atoms are used which have been prepared for example by conventional alkali catalysis from the previously mentioned low molecular weight starters and which are oligomeric alkoxylation products with (number average) molecular weights of 200 to 2,000.

Polyaddition of alkylene oxides to starter compounds which contain active hydrogen atoms catalysed by catalysts according to the invention generally takes place at temperatures from 20 to 200° C., preferably in the range 40 to 180° C., in particular at temperatures of 50 to 150° C. The reaction may be performed at total pressures of 0.001 to 20 bar. The polyaddition may be performed in bulk or in an inert, organic solvent such as toluene and/or THF. The amount of solvent is conventionally 10 to 30 wt. %, with respect to the amount of polyetherpolyol being prepared.

The catalyst concentration is chosen so that, under the given reaction conditions, effective control of the polyaddition reaction is possible. The catalyst concentration is generally in the range from 0.0005 wt. % to 1 wt. %, preferably in the range from 0.001 wt. % to 0.1 wt. %, in particular in the range from 0.001 to 0.0025 wt. % with respect to the amount of polyetherpolyol being prepared.

The number average molecular weight of the polyetherpolyols prepared by the process according to the invention is in the range from 500 to 100,000 g/mole, preferably in the range from 1,000 to 50,000 g/mole, in particular in the range from 2,000 to 20,000 g/mole.

The polyaddition reaction may be performed continuously or batchwise, e.g. in a batch or semi-batch process.

Catalysts according to the invention may be used in very low concentrations (25 ppm and lower, with respect to the amount of polyetherpolyol being prepared) due to their greatly increased activity. If polyetherpolyols prepared in the presence of catalysts according to the invention are used to prepare polyurethanes (Kunststoffhandbuch, Vol. 7, Polyurethane, 3rd Edition, 1993, p. 25–32 and 57–67), there is no need to remove the catalyst from the polyetherpolyol and this does not have a detrimental effect on the product quality of the polyurethane obtained.

EXAMPLES

Catalyst Preparation

Example A

Preparing a DMC Catalyst Using the Sodium Salt of Cholic Acid (Catalyst A)

A solution of 6.2 g (45.75 mmol) of zinc chloride in 10 ml of distilled water is added to a solution of 2 g (6 mmol) of potassium hexacyanocobaltate in 35 ml of distilled water with vigorous stirring (24,000 rpm). Immediately afterwards, a mixture of 25 g of tert-butanol and 25 g of distilled water is added to the suspension produced and then stirred vigorously (24,000 rpm) for 10 min. Then a mixture of 0.5 g of the sodium salt of cholic acid (Fluka Chemie AG, CH-9471 Buchs), 0.5 g of tert-butanol and 50 g of distilled water is added and stirring is continued for 3 min (1,000 rpm). The solid is isolated by filtration, then stirred (10,000 rpm) for 10 min with a mixture of 35 g of tert-butanol, 15 g of distilled water and 0.5 g of the sodium salt of cholic acid and filtered again. Then the product is stirred once again (10,000 rpm) for 10 min with a mixture of 50 g of tert-butanol and 0.25 g of the sodium salt of cholic acid. After filtration, the catalyst is dried to constant weight at 50° C. and atmospheric pressure.

Yield of dry, powdered catalyst: 2.1 g

Elemental analysis, thermogravimetric analysis and extraction:

Cobalt=12.6 wt. %, zinc=27.3 wt. %, tert-butanol=10.9 wt. %, sodium salt of cholic acid=4.3 wt. %.

Example B

Preparing a DMC Catalyst Using the Sodium Salt of Hyodeoxycholic Acid (Catalyst B)

The same procedure was used as described in example A, but the sodium salt of hyodeoxycholic acid (Sigma-Aldrich Chemie GmbH, D-82041 Deisenhofen) was used instead of the sodium salt of cholic acid from example A.

Yield of dry, powdered catalyst: 2.0 g

Elemental analysis, thermogravimetric analysis and extraction:

Cobalt=13.8 wt. %, zinc=28.3 wt. %, tert-butanol=7.3 wt. %, sodium salt of hyodeoxycholic acid=6.2 wt. %.

Example C (Comparison Example)

Preparing a DMC catalyst using tert-butanol without a bile acid or its salt, ester or amide (catalyst C, synthesis in accordance with JP-A 4145123)

A solution of 10 g (73.3 mmol) of zinc chloride in 15 ml of distilled water is added to a solution of 4 g (12 mmol) of potassium hexacyanocobaltate in 75 ml of distilled water with vigorous stirring (24,000 rpm). Immediately afterwards, a mixture of 50 g of tert-butanol and 50 g of distilled water is added to the suspension produced and then stirred vigorously (24,000 rpm) for 10 min. The solid is isolated by filtering, then stirred (10,000 rpm) for 10 min with 125 g of a mixture of tert-butanol and distilled water (70/30; w/w) and filtered again. The product is then stirred again (10,000 rpm) for 10 min with 125 g of tert-butanol. After filtration, the catalyst is dried to constant weight at 50° C. and atmospheric pressure.

Yield of dry, powdered catalyst: 3.08 g

Elemental analysis:

Cobalt=13.6 wt. %, zinc=27.4 wt. %, tert-butanol=14.2 wt. %.

Preparing Polyetherpolyols

General Method 50 g of polypropylene glycol starter (molecular weight=1,000 g/mol) and 3 to 5 mg of catalyst (15 to 25 ppm, with respect to the amount of polyetherpolyol being prepared) are initially introduced into a 500 ml pressurised reactor under a protective gas (argon) and heated to 105° C. with stirring. Then propylene oxide (ca. 5 g) is added in one portion until the total pressure has increased to 2.5 bar. Further propylene oxide is only added when an accelerated pressure drop is observed in the reactor. This accelerated pressure drop indicates that the catalyst has been activated. Then the remainder of the propylene oxide (145 g) is added continuously at a constant total pressure of 2.5 bar. After addition of all the propylene oxide and a 2 hour post-reaction period at 105° C., volatile components are distilled off at 90° C. (1 mbar) and the mixture is then cooled to room temperature.

The polyetherpolyols obtained were characterised by determining the OH values, the double bond content and the viscosities.

The reaction was followed by means of a time/conversion curve (propylene oxide consumption [g] versus reaction time [min]). The induction time was determined from the point of interception of the tangent to the steepest point of the time/conversion curve with the extended base line of the curve. The propoxylation times which are critical for catalyst activity correspond to the period between catalyst activation (end of the induction period) and the end of propylene oxide addition. The total reaction time is the sum of the induction and propoxylation times.

Example 1

Preparing polyetherpolyol with Catalyst A (25 ppm)

| | |
|---|---|
| Induction time: | 217 min |
| Propoxylation time: | 33 min |
| Total reaction time: | 250 min |
| Polyetherpolyol: OH value (mg of KOH/g): | 29.6 |
| Double bond content (mmol/kg): | 6 |
| Viscosity at 25° C. (mPas): | 855 |

Example 2

Preparing Polyetherpolyol with Catalyst A (15 ppm)

| | |
|---|---|
| Induction time: | 387 min |
| Propoxylation time: | 168 min |
| Total reaction time: | 555 min |
| Polyetherpolyol: OH value (mg of KOH/g): | 30.1 |
| Double bond content (mmol/kg): | 6 |
| Viscosity at 25° C. (mPas): | 993 |

Without removing the catalyst the metal content in the polyol was: Zn=4 ppm, Co=2 ppm.

Example 3

Preparing Polyetherpolyol with Catalyst B (25 ppm)

| | |
|---|---|
| Induction time: | 371 min |
| Propoxylation time: | 40 min |
| Total reaction time: | 411 min |
| Polyetherpolyol: OH value (mg of KOH/g): | 30.2 |
| Double bond content (mmol/kg): | 6 |
| Viscosity at 25° C. (mPas): | 902 |

Example 4 (Comparison Example)

Catalyst C (15 ppm) exhibited no activity at all under the reaction conditions described above even after 14 hours induction time.

When using 50 ppm of catalyst C, the induction time was about 9 hours. The propoxylation time was more than 12 hours, wherein catalyst deactivation occurred during the course of the reaction.

Examples 1–3 show that the new DMC catalysts according to the invention can be used in such small concentrations during the preparation of polyetherpolyols, due to their greatly increased activity, that separation of the catalyst from the polyol is not required.

What is claimed is:

1. A double-metal cyanide catalyst comprising:
   a) at least one double-metal cyanide compound;
   b) at least one organic complex ligand which is not a bile acid, a bile acid salt, a bile acid ester or a bile acid amide; and
   c) at least one bile acid, bile acid salt, bile acid ester or bile acid amide.

2. The double-metal cyanide catalyst according to claim 1, further comprising water and/or one or more water soluble metal salts.

3. The double-metal cyanide catalyst according to claim 1, wherein the double-metal cyanide compound is zinc hexacyanocobaltate (III).

4. The double-metal cyanide catalyst according to claim 1, wherein the organic complex ligand comprises an alcohol, aldehydes, ketone, ether, ester, amide, urea, nitrile, sulfide and/or a mixture thereof.

5. The double-metal cyanide catalyst according to claim 1, wherein the organic complex ligand is tert-butanol.

6. The double-metal cyanide catalyst according to claim 1, wherein the bile acid, bile acid salt, bile acid ester or bile acid amide is present in an amount of from about 1 to about 80 wt. %, based on the amount of finished double-metal cyanide catalyst.

7. The double-metal cyanide catalyst according to claim 1, wherein the bile acid, bile acid salt, bile acid ester or bile acid amide is present in an amount of from about 1 to about 40 wt. %, based on the amount of finished double-metal cyanide catalyst.

8. The double-metal cyanide catalyst according to claim 1, wherein the bile acid salt is the sodium, lithium or potassium salt or the methyl or ethyl ester of cholic acid, glycocholic acid, taurocholic acid, deoxycholic acid, glycodeoxycholic acid taurodeoxycholic acid, chenodeoxycholic acid, glycochenodeoxycholic acid, taurochenodeoxycholic acid, lithocholic acid, hyocholic acid, hyodeoxycholic acid or a mixture thereof.

9. A process for the preparation of a double-metal cyanide catalyst according to claim 1, comprising the steps of: (a) reacting, in aqueous solution, (i) at least one metal salt, (ii) with at least one metal cyanide salt, in the presence of (iii) an organic complex ligand, which is not a bile acid, bile acid salt, bile acid ester or bile acid amide, to form a suspension; and (b) treating the suspension with at least one bile acid, bile acid salt, bile acid ester or bile acid amide.

10. A process according to claim 9, further comprising the steps of: (c) isolating the catalyst from suspension after (b); (d) washing the isolated catalyst; and (e) drying the isolated catalyst.

11. A process for the production of a polyether polyol by polyaddition of an alkylene oxide onto a starter compound containing active hydrogen atoms in which the polyaddition of alkylene oxide is conducted in the presence of the double-metal cyanide catalyst of claim 1.

12. A double-metal cyanide catalyst according to claim 1, wherein the double-metal cyanide catalyst is used for the production of a polyether polyol by polyaddition of an alkylene oxide onto a starter compound having active hydrogen atoms.

13. A double-metal cyanide catalyst comprising:
   a) at least one double-metal cyanide compound;
   b) at least one organic complex ligand which is not a bile acid, a bile acid salt, a bile acid ester or a bile acid amide; and
   c) at least one bile acid, bile acid salt, bile acid ester or bile acid amide, wherein the bile acid is represented by the formula:

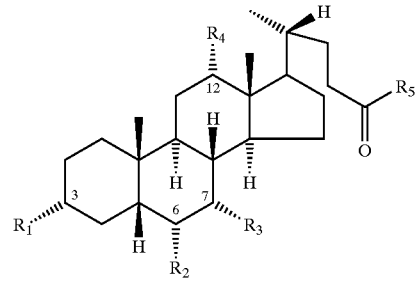

wherein
$R_1$, $R_2$, $R_3$, $R_4$, independently, represent H or OH and
$R_5$ represents OH, $NH-CH_2-CH_2-SO_3H$, $NH-(CH_2)_3-N^+(CH_3)_2-(CH_2)_3$, $-SO_3$, $NH-(CH_2)_3-N^+(CH_3)_2-CH_2-CHOH-CH_2-SO_3^-$ or $NH-CH_2-COOH$.

14. The double-metal cyanide catalyst according to claim 13, further comprising water and/or one or more water soluble metal salts.

15. The double-metal cyanide catalyst according to claim 13, wherein the double-metal cyanide compound is zinc hexacyanocobaltate (III).

16. The double-metal cyanide catalyst according to claim 13, wherein the organic complex ligand comprises an alcohol, aldehydes, ketone, ether, ester, amide, urea, nitrile, sulfide and/or a mixture thereof.

17. The double-metal cyanide catalyst according to claim 13, wherein the organic complex ligand is tert-butanol.

18. The double-metal cyanide catalyst according to claim 13, wherein the bile acid, bile acid salt, bile acid ester or bile acid amide is present in an amount of from about 1 to about 80 wt. %, based on the amount of finished double-metal cyanide catalyst.

19. The double-metal cyanide catalyst according to claim 13, wherein the bile acid, bile acid salt, bile acid ester or bile acid amide is present in an amount of from about 1 to about 40 wt. %, based on the amount of finished double-metal cyanide catalyst.

* * * * *